United States Patent [19]

Imai et al.

[11] Patent Number: 5,211,829

[45] Date of Patent: May 18, 1993

[54] ANALYTICAL METHOD AND APPARATUS USING CAPILLARY TUBE

[75] Inventors: Kazumichi Imai; Masataka Koga, both of Katsuta; Takehiko Kitamori, Ushiku; Tsuguo Sawada; Jiaqi Wu, both of Tokyo, all of Japan

[73] Assignee: Hitachi, Ltd., Tokyo, Japan

[21] Appl. No.: 664,604

[22] Filed: Mar. 4, 1991

[30] Foreign Application Priority Data

Mar. 2, 1990 [JP] Japan .................................. 2-049315

[51] Int. Cl.$^5$ .................. G01N 27/26; G01N 27/447; G01N 21/85
[52] U.S. Cl. ............................ 204/299 R; 204/180.1; 73/61.58
[58] Field of Search ........................ 204/180.1, 299 R; 73/23.4, 24.02, 61.58

[56] References Cited

U.S. PATENT DOCUMENTS 4,602,989 7/1986 Culkin ............................... 204/180.1
4,909,919 3/1990 Morris ............................... 204/180.1
4,940,333 7/1990 Pawliszyn ........................... 356/128

OTHER PUBLICATIONS

Laser-Induced Capillary Vibration for Ultramicroanalysis, Wu et al—Analytical Chemistry—1990 vol. 62, No. 15.
Photoacoustic Immunoassay Using Sensitivity Size Dependency For Determination of Turbid Solutions, Kitamori et al—Analytical Chemistry, 1987—vol. 59, No. 20.

Primary Examiner—John Niebling
Assistant Examiner—John S. Starsiak, Jr.
Attorney, Agent, or Firm—Antonelli, Terry, Stout & Kraus

[57] ABSTRACT

The present invention is applied to an analyzer according to which a sample to be analyzed is moved through a capillary tube in liquid chromatography or capillary-zone electrophoretic method. The capillary tube has a separation zone and a detection zone. The capillary tube in the detection zone has a section in which it can vibrate and both ends of this section are fixed.

Analytes of the sample introduced into the analyzer are separated from each other in the separation zone. When each of the separated analytes is led to the area irradiated with beam in the detection zone, the capillary tube in the detection zone vibrates. This vibration phenomenon is brought about by tension fluctuation of the capillary tube caused by intermittent irradiation of the detection zone with an excitation beam and absorption of the excitation beam by the analyte. Concentration of analytes in the sample can be measured by detecting amplitude of the vibration.

20 Claims, 7 Drawing Sheets

ANALYTICAL METHOD AND APPARATUS USING CAPILLARY TUBE

BACKGROUND OF THE INVENTION

The present invention relates to an analytical method and an analytical apparatus which use a capillary tube and especially to an analytical method and an apparatus suitable for measuring samples or analytes separated in a capillary tube for separation.

Separation analytical methods such as the electrophoretic method and chromatography are widely used for analyzing and measuring a slight amount of substance contained in liquid or gas test samples. Recently, capillary tubes have been employed as a means to carry out separation of a sample in these separation analytical methods in order that a substance contained at low concentration in a slight amount of sample can be measured.

Various detection methods have also been proposed in gas chromatography and liquid chromatography for detection of analytes separated by a separation capillary tube. Especially, research on a new detection method has been effected in capillary-zone electrophoresis (hereinafter referred to as "CZE"). For example, a capillary-zone electrophoresis which detects the separated analytes by placing a work electrode of an electrochemical detector downstream the separation capillary tube is disclosed in "Analytical Chemistry", vol. 61, pp. 292A–303A (1989). Furthermore, a capillary-zone electrophoresis which measures thermal changes based on the sample in a capillary tube using a probe beam by irradiating the separation capillary tube per se with an excitation laser beam and a probe laser beam is disclosed in "Applied Spectroscopy", vol. 43, pp. 196–201 (1989).

According to the method which uses a conventionally generally employed detector, the analyte separated by capillary tube is led to the detector through a flow path and there occurs reduction in resolving power for separation of analyte because the analyte is taken out of the capillary tube.

Furthermore, in the method of the first reference cited above, since a high-voltage current source necessary for separation operation and a detection system must be electrically isolated, a connection structure comprising a porous glass provided between the outlet end of separation capillary tube and the inlet end of flow path in detection system is employed and thus, resolving power unavoidably reduces owing to the presence of the connection part. Furthermore, detection sensitivity is not sufficient. The method of the second reference cited above employs a construction which detects a change in refractive index caused by expansion of the sample liquid per se which undergoes thermal change by excitation beam and, besides, detects the probe beam which has passed through the sample in the capillary tube. Therefore, the measured value is affected by scattering and reflection of the probe beam at the surface of capillary tube.

SUMMARY OF THE INVENTION

An object of the present invention is to provide an anlytical method and an analytical apparatus for measurement of a sample in a capillary tube based on a new measurement theory.

Another object of the present invention is to provide an analytical method and an analytical apparatus which use a capillary tube and which can carry out measurement of a sample with sensitivity much higher than that of the conventional technique.

The present invention is characterized in that a capillary tube in which a sample is contained is irradiated with an intensity-modulated beam or an intermittent beam to produce vibration and the information based on the vibration of the capillary tube is detected, to thereby measure the sample.

DETAILED DESCRIPTION OF THE PREFERRED EMBODIMENTS

Figure 1:
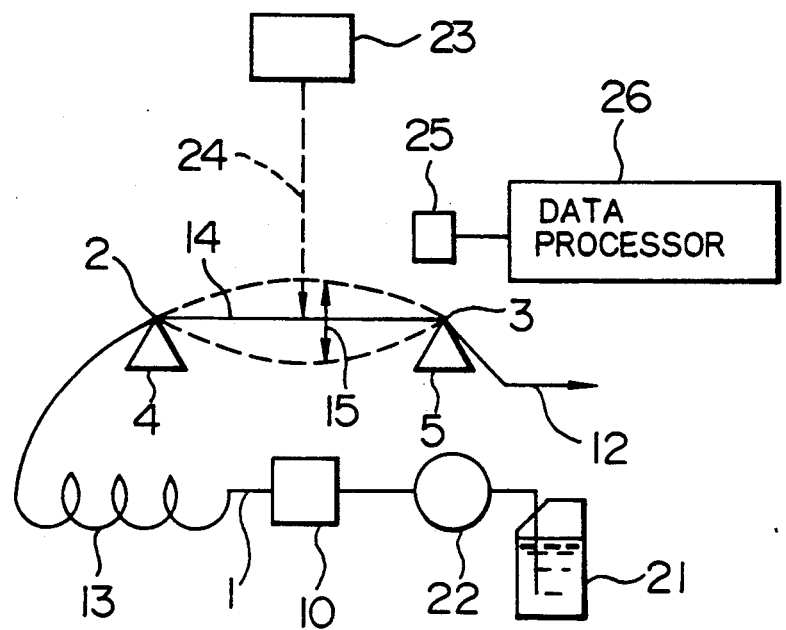
FIG. 1 is a block diagram which shows construction of one example of the present invention.

Prior to explanation of some examples based on the present invention, explanation will be made on characteristics of the analytical apparatus which employs the present invention.

One long capillary tube has a separation zone having a function to separate analytes in the sample from each other and a detection zone for detection of each analyte separated. The detection zone is supported so that the capillary tube can vibrate. In place of using one long capillary tube, a tube for separation zone and a tube for detection zone may be connected in series. The separation zone is connected to a sample injection port and the detection zone is arranged so that it communicates with a sample output.

In the detection zone, the capillary tube is supported by holders so that it does not move at both ends of that section. With reference to the size of the capillary tube, the inner diameter is 1 mm or less and the outer diameter is 2 mm or less. Material of the capillary tube is one which is as small as possible in absorption of light and, for example, fused silica or silica glass is selected.

An excitation beam formed to have a cross-section of a given size is projected to the abovementioned section of capillary tube. The size of cross-section of this beam is far smaller than the length of that section. The excitation beam is modulated in its intensity or switched on or off at a given period. Within the above section, the capillary tube is supported so that it does not slacken. When a band of sample or separated analyte enters the detection section of the capillary tube and reaches the area irradiated with the excitation beam, the sample absorbs the excitation beam and is heated. The heating state is lowered while the excitation beam is off. On and off of the excitation beam are carried out periodically many times until the sample has passed through the irradiated area in the capillary tube, whereby repetition of heat fluctuation also periodically occurs. Accordingly, tension fluctuates in the detection section of the capillary tube, especially the area irradiated with excitation beam and the capillary tube vibrates in the similar manner to mechanical vibration of a string.

Intensity of vibration, namely, amplitude is substantially proportional to generated heat and furthermore, has correlation with the quantity of excitation beam absorbed by the sample. Concentration of sample or amount of analyte can be known by measuring the information based on the intensity of vibration by a proper detector. The area to be irradiated with excitation beam is preferably a center portion of the detection section of the capillary tube. One method for measuring the vibration of capillary tube is direct measurement of the vibration by a piezoelectric sensor or the like.

On the other hand, an acoustic wave is generated due to the vibration of the capillary tube. This acoustic wave can be detected by a suitable microphone or by an optical method. Further, heat generation phenomenon of analyte in the capillary tube results in periodic heat fluctuation, which propagates as a thermal wave to the outside of the capillary tube. The sample in the capillary tube can also be measured by projecting a probe beam to this thermal wave area in such a manner that it does not touch the capillary tube and detecting fluctuation (deflection) of direction of the probe beam.

EXAMPLE

FIG. 1 shows a block diagram of one example of the present invention. This example shows application of the present invention to a liquid chromatography.

In FIG. 1, the capillary tube 1 for separation of analytes is one tube from sample injection port 10 to outlet 12. The inner wall of capillary tube 1 is coated with a stationary liquid for liquid chromatography. Detection zone or vibration zone 14 comprising a section fixed at supporting points 2 and 3 by holders 4 and 5 is formed near the outlet 12 of capillary tube 1. Here, section 13 of the capillary tube between sample injection port 10 and supporting point 2 is called an analyte separation zone. Eluent from eluent tank 21 is flowed into capillary tube 1 by liquid feeding pump 22 and discharged from outlet 12. As an elution solvent, a buffer solution containing acetonitrile, ethanol and water is used. The solution does not absorb the light having a wavelength of 266 nm.

When a very small volume (for example, 100 μl) of the sample solution is introduced into flow path from sample injection port 10 by the sample injection means, analytes are separated from each other while the band of the sample passes through capillary tube 1. The separation of analytes is completed before the band reaches supporting point 2 of separation zone 13, but separation may proceed to some degree even in detection zone 14.

Pulse beam 24 having a frequency of 1.2 kHz emitted by periodical intensity-modulated light beam emission apparatus 23 is projected to nearly the center of detection zone 14 of capillary tube 1. This pulse beam is a laser beam of 266 nm in wavelength and is an excitation beam. When the band of analyte separated in capillary tube 1 moves through detection zone 14 along the flow of eluent and reaches the area irradiated with the excitation beam at the center of the zone, the analyte intermittently absorbs the excitation beam to cause periodical heat changes, which are accompanied by generation of vibration having amplitude 15 which depends on amount of the analyte.

The acoustic wave generated by the vibration in detection zone 14 of capillary tube 1 is detected by microphone 25 provided near capillary tube 1 in such a manner that it may not contact the vibrating capillary tube 1 and the detected signal is compared with the working curve previously memorized in data processor 26 and is out-put into a display device included in the data processor 26 as a concentration value of the corresponding analyte. A silica glass tube having an inner diameter of 0.5 mm, an outer diameter of 1.0 mm and a length of 15 m is used as capillary tube 1. Outer surface of capillary tube 1 between sample injection port 10 and holder 4 is surrounded with a synthetic resin to inhibit breakage thereof. In the detection zone between holder 4 and holder 5, capillary tube 1 is usually strained so that it does not slacken. Length of this detection zone is 10 cm.

The second example in which the present invention is employed will be explained referring to FIGS. 2-5. This example shows application of the present invention to capillary-zone electrophoresis (CZE) apparatus.

One capillary tube 31 for separation containing a separation medium such as polyacrylamide gel has separation zone 32 and detection zone 33. One end of capillary tube 31 is connected to solution tank 35 which contains a buffer solution for electrophoresis and another end is connected to a buffer solution in solution tank 36. Electrodes 37 and 38 are connected to high-voltage electric source 39. Capillary tube 31 is supported at two points by the two holders 41, 42 in detector 40 and detection zone 33 of capillary tube 31 can vibrate without contacting with other members. A solution such as phosphate buffer solution or carbonate buffer solution which has less absorption of visible light of short wavelength is contained in the capillary tube.

Figure 3:
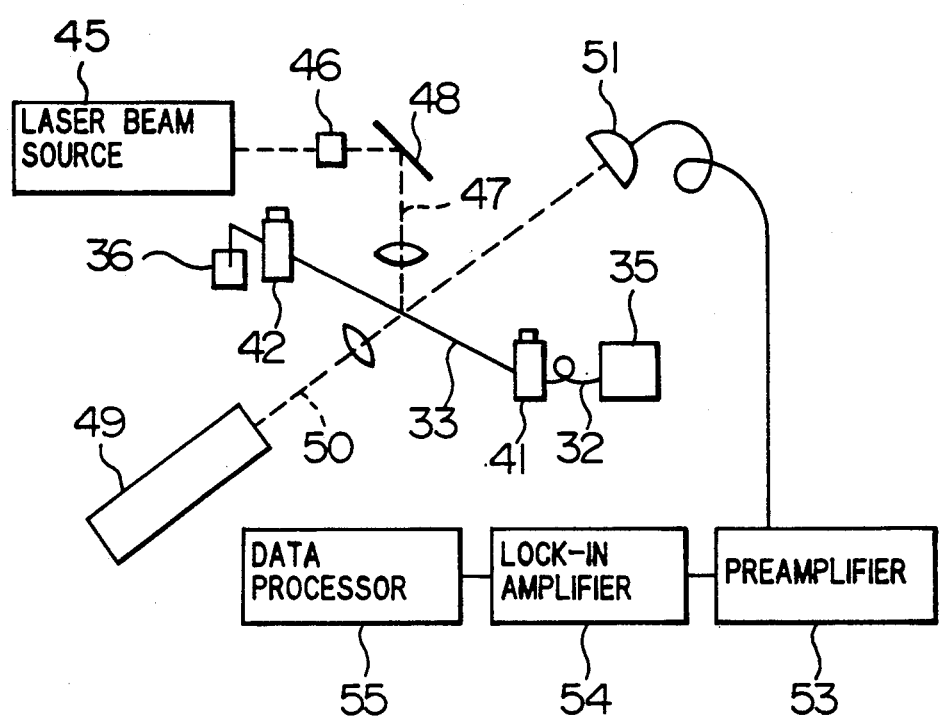
FIG. 3 is a block diagram which explains the method of detection of vibration in the analytical apparatus of FIG. 2.
Figure 4:
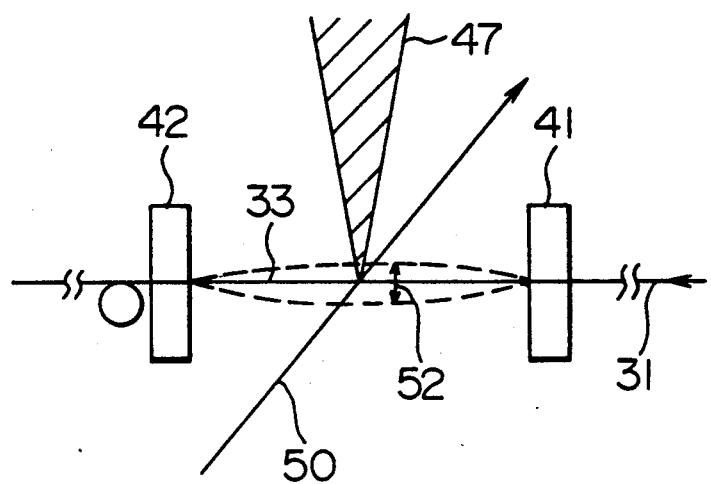
FIG. 4 is a diagram which explains the essential part of FIG. 3.

High-voltage electric source 39 which brings about separation action is set to a voltage of 20 KV. The section between sample injection port 44 of capillary tube 31 and holder 42 has a length of 50 cm. A fused silica tube of 50 μm in inner diameter and 150 μm in outer diameter is used as capillary tube 31. The volume of the sample injected is 200 pl (pico liter). The length of detection zone 33 of capillary tube 31 in the section between holders 41 and 42 is 10 cm. As shown in FIG. 3, a light beam from argon laser source 45 which is a light source for excitation is periodically modulated by intensity modulator 46 (such as a chopper) and the laser beam is projected onto the center of detection zone 33 of the capillary tube. The direction of projection of excitation beam 47 is adjusted by mirror 48.

Figure 5:
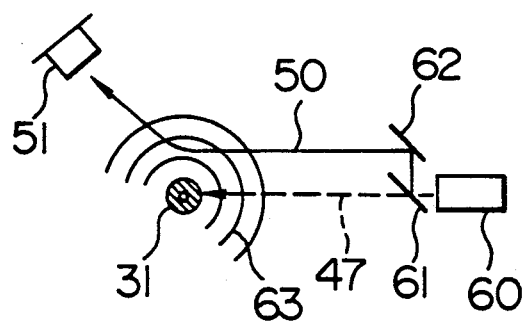
FIG. 5 is a diagram which shows the relation between excitation beam and probe beam.

Probe laser beam 50 emitted from He—Ne laser beam source 49 which constitutes a probe beam emission device is so directed that it can intersect capillary tube 31 strained in detection zone 33 at the right angle. As shown in FIG. 5, this probe beam 50 is so directed that it may not contact capillary tube 31 and it may pass through the area greatly affected by an acoustic wave generated based on the band of analyte in the capillary tube. The acoustic wave generated from the capillary tube is a compression wave and forms so-called thermal lens. This brings about a lens effect by thermal wave. The probe beam which comes near the capillary tube from light source 49 is deflected by the thermal lens effect when the analyte electrophoretically separated reaches the excitation beam irradiated area in the detection zone of capillary tube 31. Angle of deflection of the probe beam 50 is proportional to intensity of the thermal wave. Thus, the amount of sample in the capillary tube can be measured by measuring the angle of deflection by photodiode array 51.

In FIG. 3, only one array-shaped photoelectric detector 51 which detects the angle of deflection of probe beam 50 is provided, but a plurality of the detectors may be provided. A signal from photoelectric detector 51 is recorded in the recorder of data processor 55 through preamplifier 53 and lock-in amplifier 54. Irradiation with periodically intensity modulated excitation beam 47 results in vibration of detection zone 33 of capillary tube 31 which has an amplitude 52 corresponding to the concentration of the analyte. As probe laser beam 50, one which has a wavelength of 633 nm is used here. The wavelength of the excitation beam can be selected depending on kind of the sample, but two wavelengths of 488 nm and 458 nm are used here. The output power of laser beam source 45 is 70 mW. Modulation frequency by light beam intensity modulator 46 is set at 1.2 KHz.

Figure 9A:
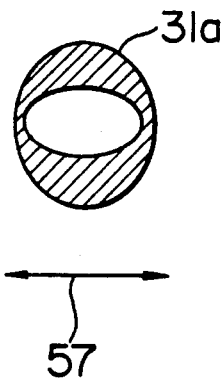
FIGS. 9A and B show cross-sectional structures of capillary tubes, respectively.
Figure 9B:
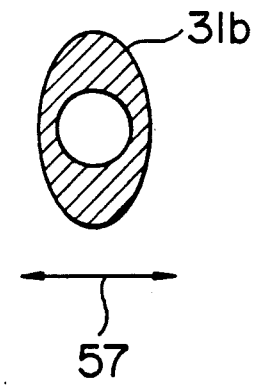

As the excitation beam source, a xenon lamp or a mercury lamp of high output power may also be used. Vibration movement of the capillary tube is ideally in the direction parallel to the direction of irradiation of excitation beam 47 and is a planar movement and in order to ensure the movement capillary tube 31 preferably has a cross-sectional shape as shown in FIG. 9. That is, capillary tube 31a having such an outer diameter as to form a substantially complete circle and such an inner diameter as to form a flat circle as shown in FIG. 9A or capillary tube 31b having such an outer diameter as to form a flat circle and such an inner diameter as to form a substantially complete circle as shown in FIG. 9B is used. In that case, expectable vibration direction 57 is parallel to the direction of the counterposed thin sections of capillary tubes 31a and 31b and is perpendicular to the direction of the counterposed thick sections and thus this fact should be taken into consideration when the capillary tube is provided.

In FIG. 3, the direction of excitation beam 47 and that of probe beam 50 are made to intersect each other at the right angle, but the light beams are not limited to this directional relationship. FIG. 5 shows another directional relationship, in which excitation beam 47 and probe beam 50 are projected in parallel to each other. In FIG. 5, the beam from light source 60 is divided into two by half mirror 61 and one of the beams hits capillary tube 31 as excitation beam 47. The other is directed to thermal lens 63 by reflector 62 as probe beam 50 and the deflected probe beam is detected by photodiode detector 51.

Figure 2:
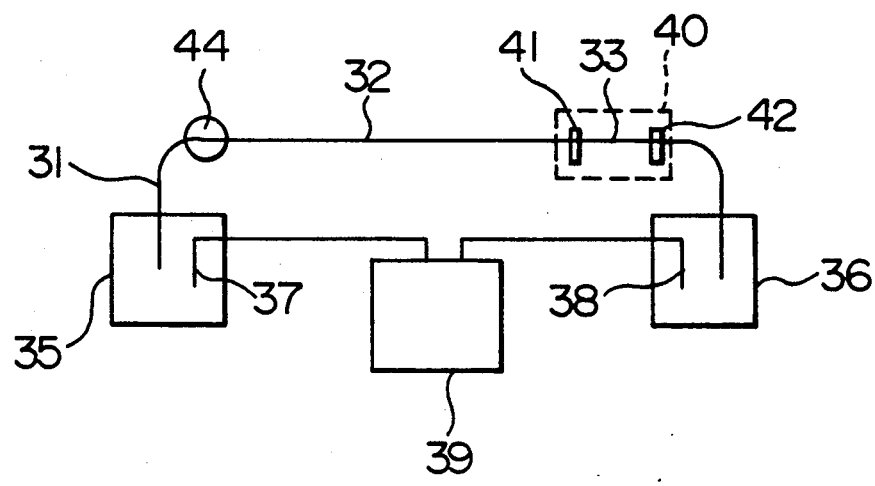
FIG. 2 is a diagram which shows a flow path system of sample according to a second example of the present invention.

An example in which an experiment was conducted using the analytical apparatus of FIG. 2 will be explained.

Figure 6:
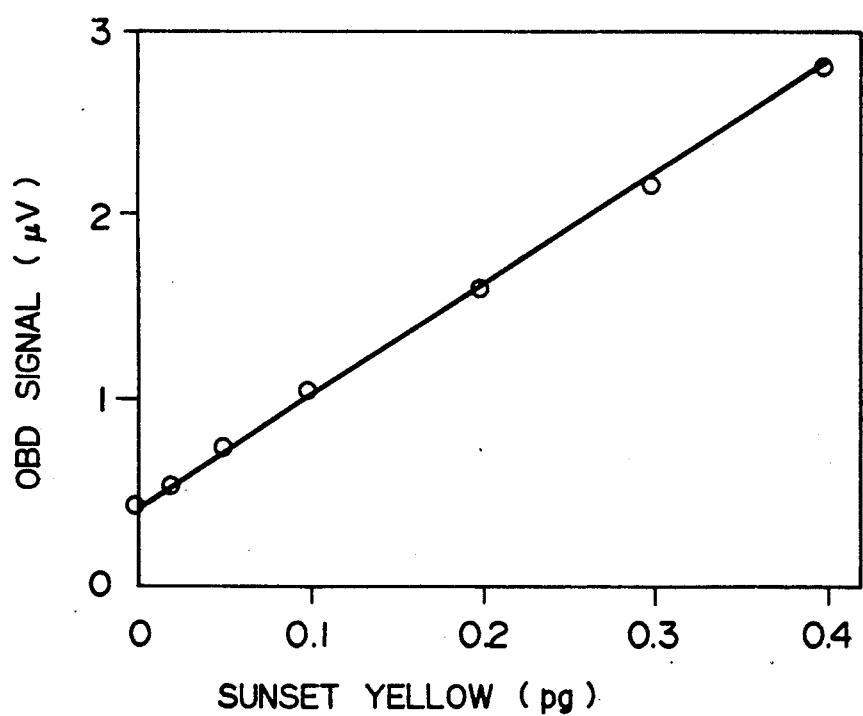
FIG. 6 is a graph which shows an example of a working curve of Sunset Yellow.

Aqueous solutions of a dye Sunset Yellow FCF (Food Yellow 3) at various concentrations were prepared as samples. Each sample was introduced into capillary tube 31 from sample injection port 44 and a working curve was prepared. The results are shown in FIG. 6 where the abscissa axis shows an amount of Sunset Yellow and the ordinate axis shows an optical beam deflection signal. The working curve shows good linearity. The limit of detection when S/N ratio was 2 was 6 fg ($6 \times 10^{-15}$ g) in terms of absolute amount of Sunset Yellow and this means a very high sensitivity.

Figure 7:
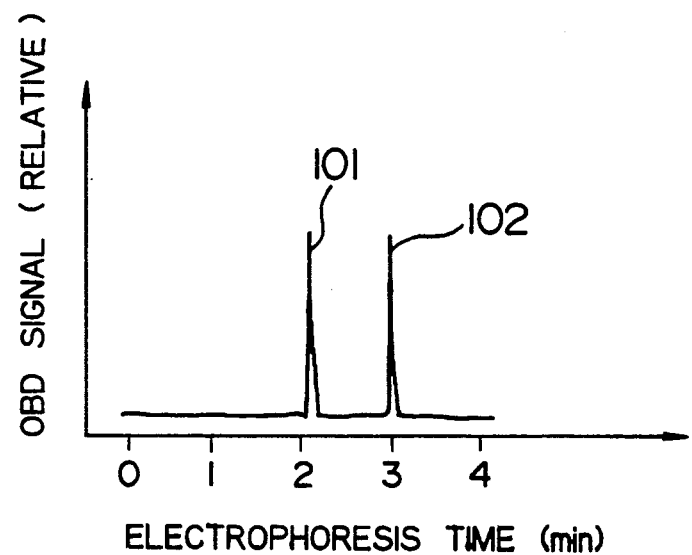
FIG. 7 shows an example of measurement of sample.

Then, electrophoretic separation was carried out using 200 pl (pico liter) of a solution containing riboflavin 101 and fluorescein sodium 102 as a sample. An example of measurement obtained by the electrophoretic separation is shown in FIG. 7. The limit of detection obtained from the working curve was 0.05 pg.

Figure 8:
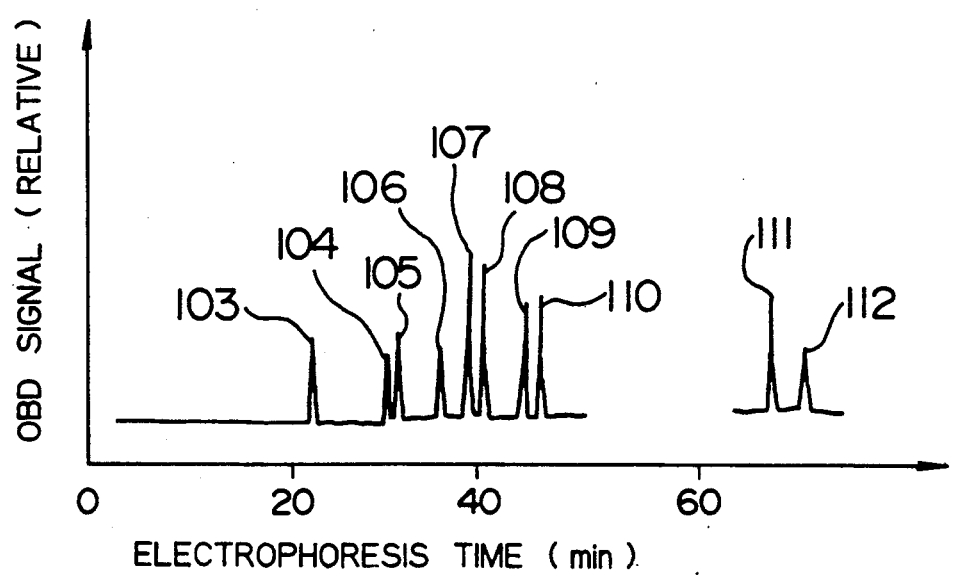
FIG. 8 shows an example of measurement of amino acid sample.

An experiment was conducted on a sample containing amino acid. An argon laser oscillation beam of 457.9 nm was used as an excitation beam. Amino acid was converted to a derivative using fluorescein isothiocyanate (FITC) or 4-(dimethylamino)azobenzene-4'-sulfonyl chloride (DABSYL chloride). An example of measurement is shown in FIG. 8. In this case, the length of capillary tube 31 between sample injection port 44 and holder 42 was 100 cm. The sample of amino acid mixture shown in FIG. 8 contained arginine 103, histidine 104, lysine 105, proline 106, leucine 107, tyrosine 108, alanine 109, glycine 110, glutamic acid 111, and aspartic acid 112.

The third example will be explained referring to FIG. 10 and FIG. 11. This third example shows application of the present invention to capillary-zone electrophoresis and is the same as the second example shown in FIG. 2 except that a means for detecting the vibration differs from the means of the second example. Only the essential parts are shown in FIG. 10.

Figure 10:
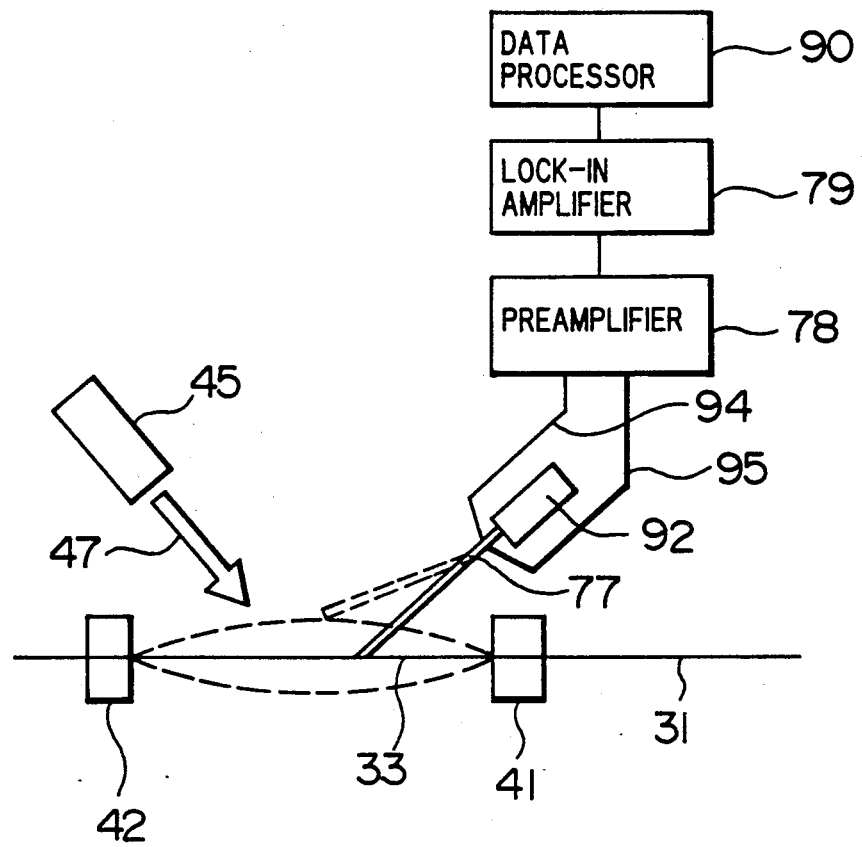
FIG. 10 is a block diagram which shows essential parts of a third example of the present invention.
Figure 11:
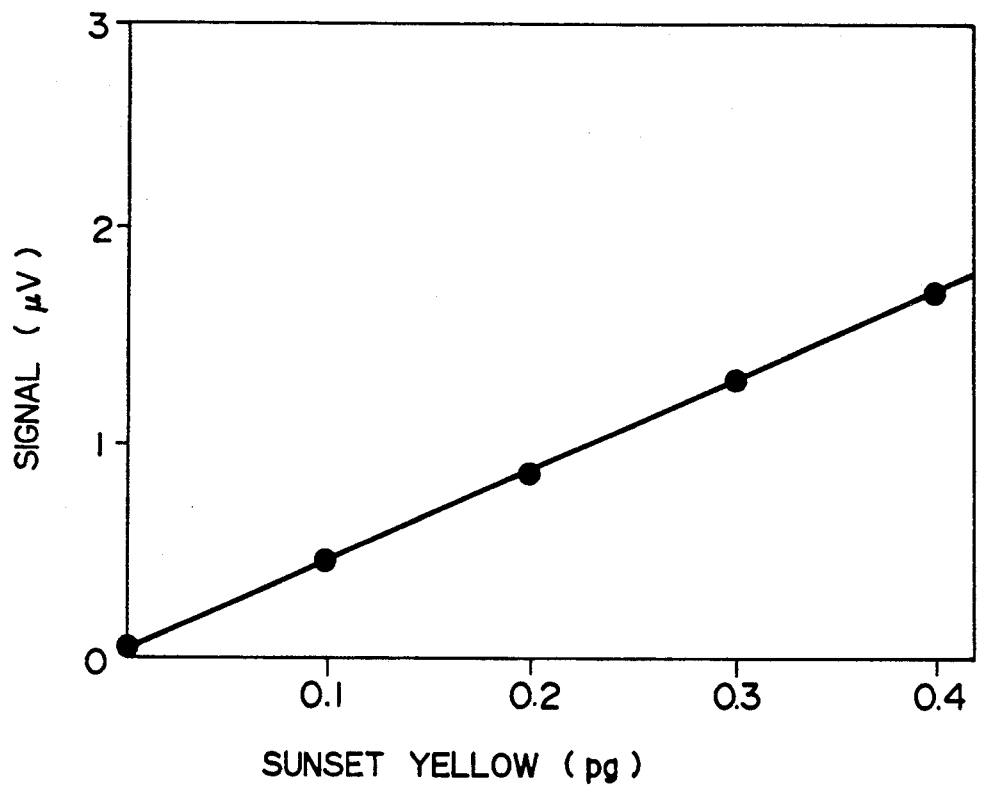
FIG. 11 is a working curve based on the example of FIG. 10.

In FIG. 10, one end of plate-like piezoelectric transducer 77 is fixed to supporting member 92. Another end of piezoelectric transducer 77 is connected to a capillary tube in detection zone 33. Therefore, piezoelectric transducer 77 acts as a means to pick up the vibration of the capillary tube induced by absorption of excitation beam 47 from light source 45 by analyte in the capillary tube. Piezoelectric transducer 77 is connected to pre-amplifier 78 through lead wires 94 and 95. The fluctuation of tension induced by vibration of the capillary tube is converted to an electric signal by piezoelectric transducer 77. The detected signal is amplified by pre-amplifier 78 and is led to data processor 90 through lock-in amplifier 79. Only the analytes which correspond to the modulated frequency of excitation beam 47 are used as data for calculation of concentration of analytes.

Piezoelectric transducer 77 is a bimorph type sensor and the main component of the element of the transducer is lead titanate zirconate $Pb(Zr \cdot Ti)O_3$. An example of a working curve obtained on Sunset Yellow using the analytical apparatus of FIG. 10 is shown in FIG. 11.

Figure 12:
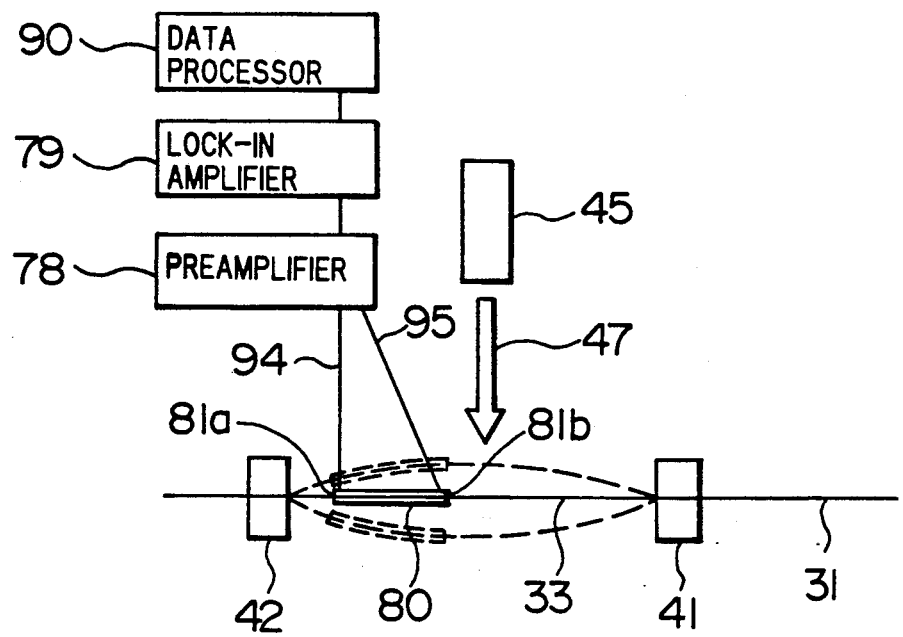
FIG. 12 is a block diagram which shows essential parts of a fourth example of the present invention.

The fourth example based on the present invention is shown in FIG. 12. In this example, the information of fluctuation of tension of the capillary tube is also detected by a piezoelectric sensor means. However, the piezoelectric sensor connected to the capillary tube in detection zone 33 in the apparatus of FIG. 12 is different type than that in FIG. 10. The film-like organic piezoelectric member 80 is provided on the surface of the capillary tube in detection zone 33 and electrodes 81a and 81b on the piezoelectric member 80 are connected to pre-amplifier 78 through lead wires 94 and 95. In this case, polyvinylidene fluoride (PVDF) which is a piezoelectric polymer is suitable as organic piezoelectric member 80.

Figure 13:
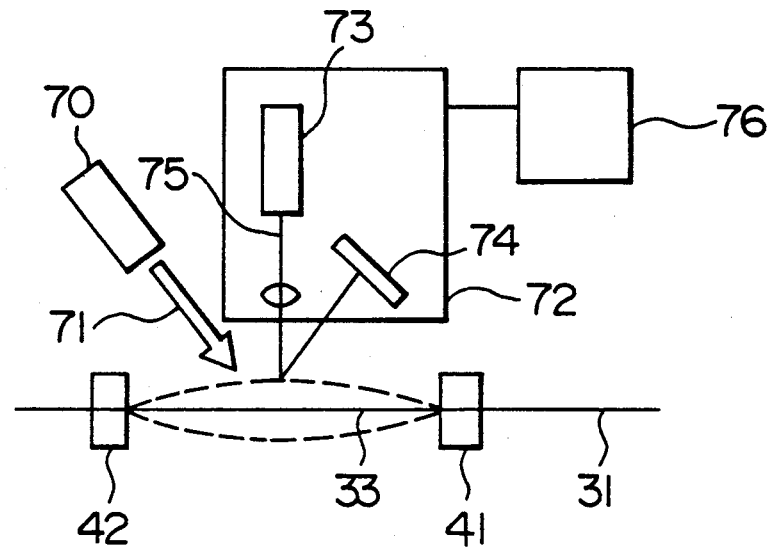
FIG. 13 is a block diagram which shows essential parts of a fifth example of the present invention.

The fifth example based on the present invention will be explained. In this example, vibration of the capillary tube is measured by a laser displacement meter. Essential parts of the capillary-zone electrophoretic apparatus are shown in FIG. 13.

YAG pulse laser beam source 70 is provided as a light source which emits excitation beam 71 and 4-fold wave (wavelength 266 nm) of the laser is used. The basic wave is 1065 nm. The pulse width is 1 ps and the repeated frequency is 1 KHz. A commercially available laser displacement meter 72 is provided as a means for detecting the vibration of the capillary tube. This displacement meter is provided with semiconductor laser beam source 73 and detector 74 and deflection of position caused by movement of the reflector can be detected by detector 74.

The irradiation beam from beam source 73 is so arranged that it may hit the capillary tube as probe beam 75 and vibration of the capillary tube is detected. The measured signal is processed by signal processing circuit 76. Displacement meter 72 is provided at a distance of 30 mm or 50 mm from capillary tube 31 in detection zone 33 so that the laser spot of displacement meter 72 may hit the capillary tube. Offset is made to zero at the state free from vibration of the capillary tube and amplitude of the vibration mode corresponding to the modulated frequency of excitation beam 71 is measured. Since the wavelength of the excitation beam is 266 nm, biochemical substances such as protein (absorption maximum 280 nm) and nucelic acid (absorption maximum 260 nm) can be subjected to measurement without pretreatments such as chemical modification.

Figure 14:
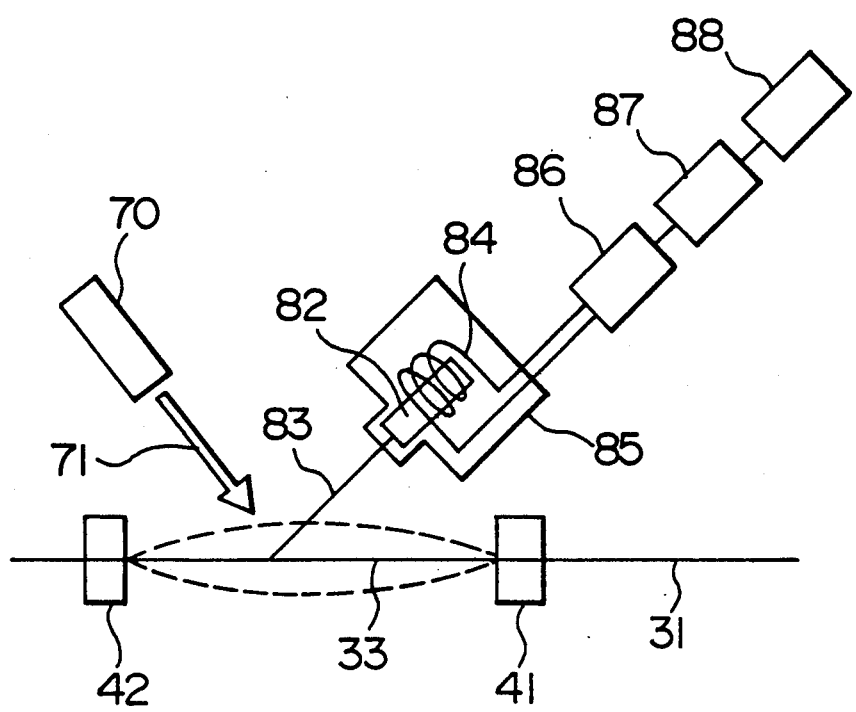
FIG. 14 is a block diagram which shows essential parts of a sixth example of the present invention.

The fifth example based on the present invention is shown in FIG. 14. In this example, induction current is measured using a moving magnet type pickup means. One end of cantilever 83 is connected to the capillary tube of detection zone. Another end of cantilever 83 is provided with magnet 82. Magnet 82 and detection coil 84 are provided in pick-up body 85. Magnet 82 is vibrated by the vibration of the capillary tube in detection zone 33 and the current thus induced in coil 84 is converted to voltage by voltage transducer 86. The signal amplified by amplifier 87 is measured by voltage detector 88.

In the above examples, the capillary tube is directly irradiated with the excitation beam, but the beam which has passed through the capillary tube is not used for measurement. Since information based on the vibration of the capillary tube is measured, the measurement is hardly affected by scattering, etc. by the capillary tube. Detection sensitivity is so high that it is possible to measure even a slight amount of substance of femto gram (fg, $10^{-15}$ g) level. Measurement can be conducted in such a state that a sample is in the capillary tube without taking the sample out from the capillary tube.

According to the present invention, measurement of high sensitivity can be attained since vibration of the capillary tube is generated and a sample in the capillary tube can be subjected to measurement on the basis of information based on the vibration.

What is claimed is:

1. An apparatus for analysis using a capillary tube which comprises:
    a capillary tube having a sample receiving position provided such that a sample can low downstream through said capillary tube from said sample receiving position,
    a capillary tube holding means which holds the capillary tube at two spaced positions thereby forming a detection zone of the capillary tube between said two spaced positions which can vibrate, said detection zone being positioned downstream of said sample receiving position,
    an irradiation means for irradiating the detection zone with a periodically intensity-modulated excitation beam or a periodical pulse-like excitation beam, and
    a detection means for detection of information based on the mechanical vibration of the capillary tube in the detection zone.

2. An apparatus according to claim 1, wherein the detection means include one of a means to detect a tension fluctuation of the capillary tube of the detection zone; a means to detect an acoustic wave resulting from the vibration; a means to detect a thermal wave generated from the sample in the capillary tube; and a means to directly detect an amplitude of the vibration.

3. An apparatus according to claim 2, wherein the means to detect the tension fluctuation includes a piezoelectric transducing means which connects to the capillary tube in the detection zone.

4. An apparatus according to claim 2, wherein the means to detect acoustic wave includes a microphone.

5. An apparatus according to claim 2, wherein the means to detect the thermal wave includes a means to detect fluctuation in direction of a probe beam by a thermal lens formed around the capillary tube, and the apparatus is provided with a means to direct the probe beam to the thermal lens.

6. An apparatus according to claim 2, wherein the means to directly detect the amplitude includes a laser displacement meter.

7. An apparatus according to claim 1, wherein outer diameter of the capillary tube is 2 mm or less.

8. An apparatus according to claim 1, wherein the capillary tube is formed to have thick sections and thin sections in its cross-section.

9. An apparatus according to claim 1, wherein the capillary tube communicates with an analyte separation zone for capillary-zone electrophoresis.

10. An apparatus according to claim 1, wherein the capillary tube communicates with an analyte separation zone for liquid chromatography.

11. An apparatus for analysis using a capillary tube which comprises:
    a capillary tube having a sample receiving position such that a sample can flow downstream through said capillary tube from said sample receiving position,
    capillary holders which hold the capillary tube at two spaced positions thereby forming a specific zone between said two spaced positions which can vibrate, said specific zone being positioned downstream of said sample receiving position,
    an irradiation device which irradiates the specific zone of the capillary tube with a periodically intensity-modulated beam or a periodical pulse beam, and
    a detection device which detects a mechanical vibration of the capillary tube in the specific zone, said mechanical vibration being induced in correspondence to the modulated frequency or intervals of irradiation time of the pulse beam.

12. An apparatus for analysis of a sample, comprising:

capillary tubing through which a sample may flow from a first end to a second end, said capillary tubing having a separation zone in which analytes in a sample can be separated downstream of said first end, and a detection zone downstream of said separation zone and upstream of said second end;

capillary tubing holders holding said capillary tubing at two spaced positions defining said detection zone therebetween, wherein said capillary tubing holders hold said capillary tubing such that said detection zone is under tension;

separation means for separating said analytes in said separation zone;

irradiation means for irradiating a portion of said detection zone with a periodically intensity-modulated excitation beam or a periodical pulse-like excitation beam; and detection means for detecting information based on mechnical vibration of said capillary tubing in said detection zone caused by periodic heat fluctuation of analytes in said detection zone due to absorption of said excitation beam by said analytes.

13. An apparatus according to claim 12, wherein said capillary tubing comprises a single capillary tube.

14. An apparatus according to claim 12, wherein said capillary tubing comprises two tubes connected in series between said separation zone and said detection zone.

15. An apparatus according to claim 12, wherein said detection means comprises a piezoelectric transducer connected to said capillary tubing and said detection zone.

16. An apparatus according to claim 12, wherein said detection means detects an acoustic wave resulting from said vibration.

17. An apparatus according to claim 12, wherein said detection means detects a thermal wave resulting from said vibration.

18. An apparatus according to claim 12, wherein said separation means comprises means for separating said analytes of said sample by capillary-zone electrophoresis.

19. An apparatus according to claim 12, wherein said separation means includes means for separating said analytes of said sample by liquid chromatography.

20. An apparatus according to claim 12, wherein at least said detection zone of said capillary tubing is made of a material selected from the group consisting of fused silica and silica glass.

* * * * *